United States Patent
Naibero et al.

(10) Patent No.: US 10,884,729 B2
(45) Date of Patent: Jan. 5, 2021

(54) METHOD AND SYSTEM FOR UPDATING OR UPGRADING FIRMWARE OF A RFID READER

(71) Applicant: Elatec GmbH, Puchheim (DE)

(72) Inventors: Antonio Naibero, Lohmar (DE);
Christian Rotzer, Munich (DE);
Dominik Samson, Taufkirchen (DE);
Stefan Haertel, Puchheim (DE)

(73) Assignee: Elatec GmbH, Puchheim (DE)

( * ) Notice: Subject to any disclaimer, the term of this patent is extended or adjusted under 35 U.S.C. 154(b) by 0 days.

(21) Appl. No.: 16/233,316

(22) Filed: Dec. 27, 2018

(65) Prior Publication Data
US 2019/0205119 A1 Jul. 4, 2019

(30) Foreign Application Priority Data
Dec. 28, 2017 (DE) .......... 10 2017 223 857

(51) Int. Cl.
*G06F 9/44* (2018.01)
*G06F 9/445* (2018.01)
(Continued)

(52) U.S. Cl.
CPC .............. *G06F 8/654* (2018.02); *G06F 8/65* (2013.01); *G06F 21/572* (2013.01);
(Continued)

(58) Field of Classification Search
CPC .......... G06F 8/654; G06F 8/65; G06F 21/572; G16H 20/17; G16H 40/63; H04W 4/80; G06K 7/10366; H04L 67/26
See application file for complete search history.

(56) References Cited

U.S. PATENT DOCUMENTS 8,892,699 B2 * 11/2014 Mann .................. G06F 8/65
709/217
8,910,868 B1 * 12/2014 Wade .................. G06K 7/0095
235/449
(Continued)

FOREIGN PATENT DOCUMENTS

DE  102009060966 A1  6/2011
DE  102012018323 A1  3/2014
WO  2009068931 A1  6/2009

OTHER PUBLICATIONS

Sovan Dalai, Microcontroller Based Remote Updating System Using Voice Channel of Cellular Network, 2015. https://ieeexplore.ieee.org/stamp/stamp.jsp?tp=&arnumber=7438154 (Year: 2015).*
(Continued)

*Primary Examiner* — Mongbao Nguyen
(74) *Attorney, Agent, or Firm* — Wood Herron & Evans LLP

(57) ABSTRACT

A method and system for updating or upgrading firmware of a RFID reader installed in an access control system are provided. The reader includes a microcontroller unit that performs method steps automatically, including checking periodically whether an update file is stored in a designated storage location. If the update file is found, the microcontroller unit reads the update file and then performs an update or upgrade process of its firmware based on the update file. The method of this invention improves use of remaining storage capacity in the RFID reader or associated devices.

15 Claims, 9 Drawing Sheets

(51) Int. Cl.

| | |
|---|---|
| *G06F 8/654* | (2018.01) |
| *G06F 8/65* | (2018.01) |
| *H04W 4/80* | (2018.01) |
| *G06F 21/57* | (2013.01) |
| *H04L 29/08* | (2006.01) |
| *G16H 20/17* | (2018.01) |
| *G16H 40/63* | (2018.01) |
| *G06K 7/10* | (2006.01) |

(52) U.S. Cl.
CPC ......... *G06K 7/10366* (2013.01); *G16H 20/17* (2018.01); *G16H 40/63* (2018.01); *H04L 67/26* (2013.01); *H04W 4/80* (2018.02)

(56) References Cited

U.S. PATENT DOCUMENTS

| | | | |
|---|---|---|---|
| 2004/0122537 A1 | 6/2004 | Kouda et al. | |
| 2007/0103303 A1* | 5/2007 | Shoarinejad | G01S 19/05 340/572.1 |
| 2009/0037899 A1 | 2/2009 | Dharap et al. | |
| 2010/0058309 A1* | 3/2010 | Lu | G06F 21/572 717/168 |
| 2010/0070966 A1 | 3/2010 | Perng et al. | |
| 2010/0169876 A1* | 7/2010 | Mann | G06F 8/65 717/170 |
| 2010/0191951 A1* | 7/2010 | Malone | G06F 9/445 713/2 |
| 2012/0180038 A1* | 7/2012 | Hu | G06F 8/654 717/173 |
| 2014/0122852 A1* | 5/2014 | Guo | G06F 9/00 713/1 |
| 2016/0294605 A1* | 10/2016 | Searle | H04L 41/082 |
| 2016/0306977 A1* | 10/2016 | Zarakas | H04L 63/123 |
| 2017/0286084 A1* | 10/2017 | Debates | G06F 8/65 |
| 2017/0344357 A1* | 11/2017 | Su | G06F 8/71 |
| 2017/0364346 A1 | 12/2017 | Peng et al. | |
| 2019/0012164 A1* | 1/2019 | Geng | G06F 8/654 |
| 2019/0026126 A1* | 1/2019 | Liu | G06F 8/654 |
| 2019/0171434 A1* | 6/2019 | Menzel | G06F 8/65 |
| 2020/0012488 A1* | 1/2020 | Koval | G06F 8/71 |

OTHER PUBLICATIONS

Ondrej Kachman, Optimized Differencing Algorithm for Firmware Updates of Low-Power Devices, 2016, pp. 1-4. https://ieeexplore.ieee.org/stamp/stamp.jsp?tp=&arnumber=7482473 (Year: 2016).*

Die Wu, R2: Over-the-Air Reprogramming on Computational RFIDs, 2016, p. 1-8. https://ieeexplore.ieee.org/stamp/stamp.jsp?tp=&arnumber=7488004 (Year: 2016).*

Alien Technology, Reader Interface Guide, 2016, pp. 1-207. https://www.ptsmobile.com/alien/Alien-Reader-Interface-Guide.pdf (Year: 2016).*

European Patent Office, Extended Suropean Search Report issued in EP Application No. 18214074.9-1224 dated May 23, 2019 (14 pages).

* cited by examiner

METHOD AND SYSTEM FOR UPDATING OR UPGRADING FIRMWARE OF A RFID READER

CROSS-REFERENCE TO RELATED APPLICATION

This application claims priority to German Patent Application No. 10 2017 223 857.7, filed Dec. 28, 2017, the entire disclosure of which is incorporated herein by reference.

TECHNICAL FIELD

The present invention relates to radio frequency identification (RFID) readers, and more specifically, to methods and systems of updating or upgrading firmware of the RFID reader.

BACKGROUND

RFID readers are becoming more and more important in applications such as physical access control or access control to devices such as electro vehicle charging stations or printers.

In many buildings, physical access control systems, so-called PACS, must be installed, as shown in one example of a known system in FIG. 1.

For example, such a system may control the access of a group of people to different parts of a building. In such physical access control systems, middleware devices, in this case door openers 8a, 8b, 8c, are connected to an access-controller 12 by a data connection 9b. Furthermore, RFID readers 1a, 1b, 1c for every door 23a, 23b, 23c are connected to the access-controller 12.

A RFID chip 10 located in a card or a token is presented to one of these readers 1a, 1b, 1c, for example to reader 1a, as shown in FIG. 1. The reader 1a checks the access data on the RFID chip 10 and, if this data corresponds to criteria for opening the respective door 23a, the door opener 8a unlocks.

To change access rights within the physical access control system 11, the access-controller 12 is generally connected to a server 14. This server 14 can be used to modify access rights which are stored in the access-controller 12. The server 14 may be a stationary server or a server in the so-called cloud 20.

Alternatively to the reader 1a, the access-controller 12 or the server 14 may verify the access rights each time a RFID chip 10 is read out by one of the readers 1a, 1b, 1c.

FIG. 2 shows another sort of known access control system 11 for controlling the access to printers 8a, 8b, 8c in a printer network. In this kind of access control system 11, each of the RFID readers 1a, 1b, 1c is connected to one of the printers 8a, 8b, 8c constituting middleware which must be controlled in this scenario via data connections 9a.

The printers 8a, 8b, 8c in turn are connected via a further data connection 9b to a printer server 14.

The printer server 14 may control access rights to each of the printers 8a, 8b, 8c of different users or RFID chips 10, preferably comprised in cards or tags.

The server 14 may be connected via a further data connection 9c to a further server 14', preferably in the cloud 20, such that access control rights can be changed, in particular granted or withdrawn, via an online application.

U.S. Patent Application Publication No. 2010/0070966 concerns a method to update firmware of a radio frequency identification (RFID) reader through a network system, where a management host issues an update message to a gateway through the network system, and then, depending upon the location where the reader firmware update data is stored, either the management host transmits the reader firmware update date through the gateway to each designated RFID reader, or the gateway directly transmits the reader firmware update data to each of the designated RFID readers. A memory microprocessor of the RFID reader stores the received reader firmware update data to a firmware data storage section of a memory unit thereof.

International PCT Patent Publication No. WO 2009/068931 concerns a method comprising receiving patch data by a contactless communication comprising a patch for a patchable firmware and patch identification information; and patching said firmware using said patch.

It would be desirable to provide a method, an RFID reader and an access control system comprising at least one such RFID reader to accomplish a simplified update or upgrade process for a firmware of an RFID reader. Furthermore, it would be desirable to provide a method for accomplishing a better storage management in an updating or upgrading process of the firmware.

SUMMARY

In one embodiment, a method is provided for updating or upgrading firmware of a radio frequency identification (RFID) reader installed in an access control system for controlling middleware. The reader has a microcontroller unit executing method steps automatically. The method includes the following steps: the microcontroller unit checks periodically whether an update file is stored in a designated storage location whose access address is predefined in a microcontroller unit; if an update file is found, the microcontroller unit reads the update file; and the microcontroller unit performs an update or upgrade process of its firmware based on the update file.

In one aspect, at least all the steps performed by the microcontroller unit of the RFID reader are executed automatically by the microcontroller unit. Within the meaning of the invention, "automatically" preferably means without any intervention by another device or user. The inventive method may be a computer-assisted method.

Within this application, an "access address" preferably is an address to access a certain location in a memory. An access address predefined in the microcontroller means that the access address is set in the microcontroller unit.

Within this application, the term "file" preferably relates to a data file or a folder, which may contain several data files.

Within this application, the term "update file" preferably is a data file or a folder containing a firmware update or a firmware upgrade. A firmware update comprises an updated firmware or at least updated parts for the existing firmware, particularly for fixing bugs in the firmware, adding new features or technologies, for example protocols. A firmware upgrade enables or disables a function that is generally available in the existing firmware, particularly for activating/deactivating or locking/unlocking radio frequencies or protocols that are per se already available in the existing firmware. The firmware upgrade may preferably be triggered by an upgrade code contained in or constituting the update file.

Within this application, the term "upgrade process" therefore is preferably a change of the settings in the firmware, whereas the term "update process" preferably comprises a step of overwriting an existing firmware and further preferably of rebooting the RFID reader comprising the microcontroller unit.

In another embodiment, a radio frequency identification reader is provided and includes a microcontroller unit, a frequency front end and a data interface, where the microcontroller unit is configured to automatically: check at a predetermined point of time, particularly periodically, via the data interface, whether an update file is stored in a designated storage location whose access address is predefined in a microcontroller unit; if an update file is found, read the update file; and perform an update process of its firmware based on the update file.

In one aspect, the checking, the reading, the performing and other actions are carried out by separate elements of the reader, particularly of the microcontroller unit.

Within this application, "means" can be formed by hardware and/or software, particularly an analog or digital central processor unit (CPU) and/or several programs or program modules. The CPU is preferably connected to a memory system and/or a data bus system. The CPU can be configured in such a manner to execute instructions which are implemented in a program stored in a memory system, to collect input signals from a data bus system and/or to produce and deliver output signals to a data bus system. A memory system can have one or several, particularly different, storage mediums, particularly RAM, optical, magnetic, solid state and/or other volatile or non-volatile mediums. A program can be configured in such a manner that it embodies or is able to execute the methods as described herein, such that a CPU can execute the steps of the methods and can control and/or monitor an update or upgrade of the firmware of an RFID reader.

In another aspect, all the elements the RFID reader are arranged on a single printed circuit board.

In yet another embodiment, an access control system is provided and includes at least one such RFID reader according to the description above and a middleware being controlled by the at least one reader.

Within this application, the term "middleware" preferably is a device to be controlled by information read out by the RFID reader.

The invention is particularly based on the idea that the firmware of an RFID reader may be updated or upgraded. The RFID readers are already installed for example in a building or in conjunction with a printer as shown in FIGS. 1 and 2. In common access control systems, these RFID readers would often have to replaced when new functionalities must be executed by the RFID readers or when the protocol or the frequency for transmitting data must be changed.

To accomplish an updating or upgrading process, according to the invention, the RFID reader itself, in particular a microcontroller unit within the reader, checks in a designated storage location whose access address is predefined in the RFID reader whether an update file is available. In one aspect, this check is done automatically, particularly periodically, by the microcontroller unit. If an update file is found, the microcontroller unit reads automatically the update file. In another aspect, the microcontroller unit then verifies if the update file contains an update or upgrade for the firmware. If the update file only does not contain an update or upgrade, the file is deleted or ignored by the microcontroller unit. If the update file contains an update or upgrade, on the contrary, the microcontroller unit preferably performs automatically an update or upgrade process of its firmware based on the read update file.

With the inventive method, an update or upgrade process of an installed RFID reader can be completely automated by just providing an update file in a predefined designated storage location. Further interaction or communication with the reader or its microcontroller unit, respectively, is not needed. The inventive method allows updating or upgrading the firmware within a plurality of RFID readers without the need to address each reader individually.

In some embodiments, the access control system includes one reader or a plurality of RFID readers and a server and/or an access-controller, where the method further includes the step of pushing an update file in the designated storage location of the at least one or the plurality of readers.

By this function, the entire set of RFID readers can be upgraded with just a single action by a network device, such as the server or the access-controller.

In one aspect, the method further includes steps of: demanding an authentication signal from the at least one reader; receiving and checking the authentication signal of the at least one reader; and only if the received authentication signal fits to a predefined scheme, loading the update file in the designated storage location of the at least one reader.

By this function, it can be guaranteed that only readers which fit a firmware update are provided with the update file.

In another aspect, the access-controller broadcasts the update file to the plurality of readers.

With this function, every reader receives the same update file effectively at the same time. Therefore, a complete rollout of a firmware or an upgrade can be accomplished.

In a further aspect, the method further includes the following steps: the microcontroller unit checking whether the content of the update file fits its firmware; and if the content fits, the microcontroller unit reading the update file and initializing the update or upgrade process; or if the content does not fit, the microcontroller unit discarding or ignoring the update file.

By this additional feature, it can be assured that only those updates or upgrades are installed on the respective RFID reader suitable for this reader.

In yet another aspect, the method further includes the steps: the microcontroller unit checking, whether the update file is larger than a first remaining space of a memory of a program memory of the microcontroller unit not being occupied by the existing operating system; if the update file is larger than the first remaining space, providing or loading an intermediate operating system file that fits in the first remaining space; the microcontroller unit performing an update process of its firmware based on the intermediate operating system file; and loading the update file in a second remaining space of the program memory of the designated storage location not being occupied by the intermediate operating system.

Otherwise, if the update file equals or is smaller than the first remaining space, the inventive method further includes the step of loading the update file in the first remaining space.

By this advantageous procedure, a storage management is provided which copes with constraints of the size of the memory of the designated storage location and assures that an update or upgrade process is not initialized with an incomplete update file. Such an incomplete update file would, in most cases, lead to a system crash of the RFID reader and most probably render the RFID reader unusable.

In one aspect, the server pushes the update file for at least one reader of the access control system in the memory of the access-controller or in the memory of a middleware, particularly serving as designated storage location, or the server pushes the update file in a memory in at least one reader serving as designated storage location, particularly via the middleware or via the access-controller.

In one alternative, the designated storage location is preferably situated in the access-controller or the middleware. By this alternative, a server has not to be directly connected to an RFID reader to be updated or upgraded. The update or upgrade process can be achieved via the data connection between an access-controller and the respective RFID reader or between the middleware and the respective RFID reader. In another option, the access-controller or the middleware itself pushes or sends the update file, after receiving the same from the server, to a designated storage location in the RFID reader. This first alternative is especially advantageous since the RFID reader to be upgraded or updated does not need to have a further data connection to the server. In the second alternative the server pushes the update file directly to the RFID reader. In this second alternative embodiment, there is no need for a data connection between an access-controller or a middleware and the RFID reader to be upgraded or updated. This may be advantageous for example in cases where an access-controller or a middleware are not connected to the cloud or the internet.

In some embodiments, the at least one reader is connected by a wireless data connection, particularly a long-range radio network, preferably a LORA and/or a mobile communication protocol, to the server, particularly a cloud server, in a client-server-architecture.

In other embodiments, the method further includes the step: the at least one reader sending assignments to firmware controlled by the readers via the server.

In this embodiment, not only can the RFID readers be updated or upgraded directly via a data connection, preferably wireless, the server, but also instructions to the middleware controlled by the readers are sent by the intermediary of the data connection to the server.

In a further embodiment, the method further includes the step: at least one of the readers distributing the update file to the other readers in the access-control system.

This embodiment especially applies in so-called mesh networks, where one of the readers receives the update file and the readers then distribute the update file amongst each other.

In one aspect, the designated storage location is a memory in the reader, particularly a memory in the microcontroller unit.

Such a reader is easy to build. Preferably, the designated storage location is a memory that is included in the CPU element soldered to a printed circuit board. Further preferably, standard elements can be used to build up such a reader.

In another aspect, the designated storage location is a dedicated additional storage element connected to the microcontroller unit, particularly an external EEPROM or Flash memory.

In this embodiment, a relatively cheap microcontroller with a small memory, particularly program memory, can be used. The reader can then be a standardized reader for a lot of applications and only those readers which need to have an update or upgrade capability are equipped with the external memory, particularly on a printed circuit board. This reduces the overall production costs of the reader due to scaling effects.

In a further aspect, the designated storage location is a memory in middleware, particularly a printer, connected by a data connection to the reader and being controlled by the reader.

This embodiment has the advantage that a data connection between a server and the cloud or the internet and the middleware can be controlled by the middleware. Furthermore, the middleware does not have to have further functions for forwarding an update file to the reader. All the updating processes can be then automatically performed by the RFID reader itself.

In yet another aspect, the data interface is configured to communicate in a long-range radio network, preferably a LORA and/or a mobile communication protocol.

By these different interfaces, a direct connection to a server may be established between the reader and the server. For example, the data connection between a server and the reader can be established for example by a mobile device, wherein the mobile device is in the proximity of the reader and provides a remote data connection to the server via a mobile device data protocol.

In another embodiment, the inventive access-control system further comprises an access-controller, particularly a physical access-controller, which is connected to the plurality of readers via a data connection, particularly using the Open Supervised Device Protocol (OSDP) or the RS485 protocol or TCP/IP protocol or similar other protocols.

In one aspect, the designated storage location is a memory in the access-controller or a memory in the middleware.

By this arrangement, the respective RFID reader can fully automatically execute an update process for its firmware without the need to provide a special function for pushing an update file to the RFID reader in the access-controller and/or the middleware.

In another aspect, the at least one reader is configured to act as an access point for a mesh-network between a plurality of readers.

In this embodiment, not every RFID reader in an access-control system needs to have data connection to the designated storage location for example situated in the middleware, in an access-controller or in a server.

In yet another aspect, the server is connected by data connection directly to the at least one reader via the data interface or by a data connection to an access-controller, wherein the designated storage location is a memory of the server.

If the RFID reader can directly communicate with the server, the access-controller or the accesses controllers of the access-control system can be built relatively cheap with a minimum of memory.

In a further aspect, the access-controller has a wireless module, particularly Wi-Fi, Bluetooth or NFC, etc., and the data connection between the server and the access-controller is established via the wireless module.

With this further embodiment, the data connection between a server and the access-controller can be established for example by a mobile device, wherein the mobile device is in the proximity of the access-controller and provides a remote data connection to the server via a mobile device data protocol.

BRIEF DESCRIPTION OF THE DRAWINGS

Various additional features and advantages of the invention will become more apparent to those of ordinary skill in the art upon review of the following detailed description of one or more illustrative embodiments taken in conjunction with the accompanying drawings. The accompanying drawings, which are incorporated in and constitute a part of this specification, illustrates one or more embodiments of the invention and, together with the general description given above and the detailed description given below, explains the one or more embodiments of the invention.

DETAILED DESCRIPTION

Figure 1:
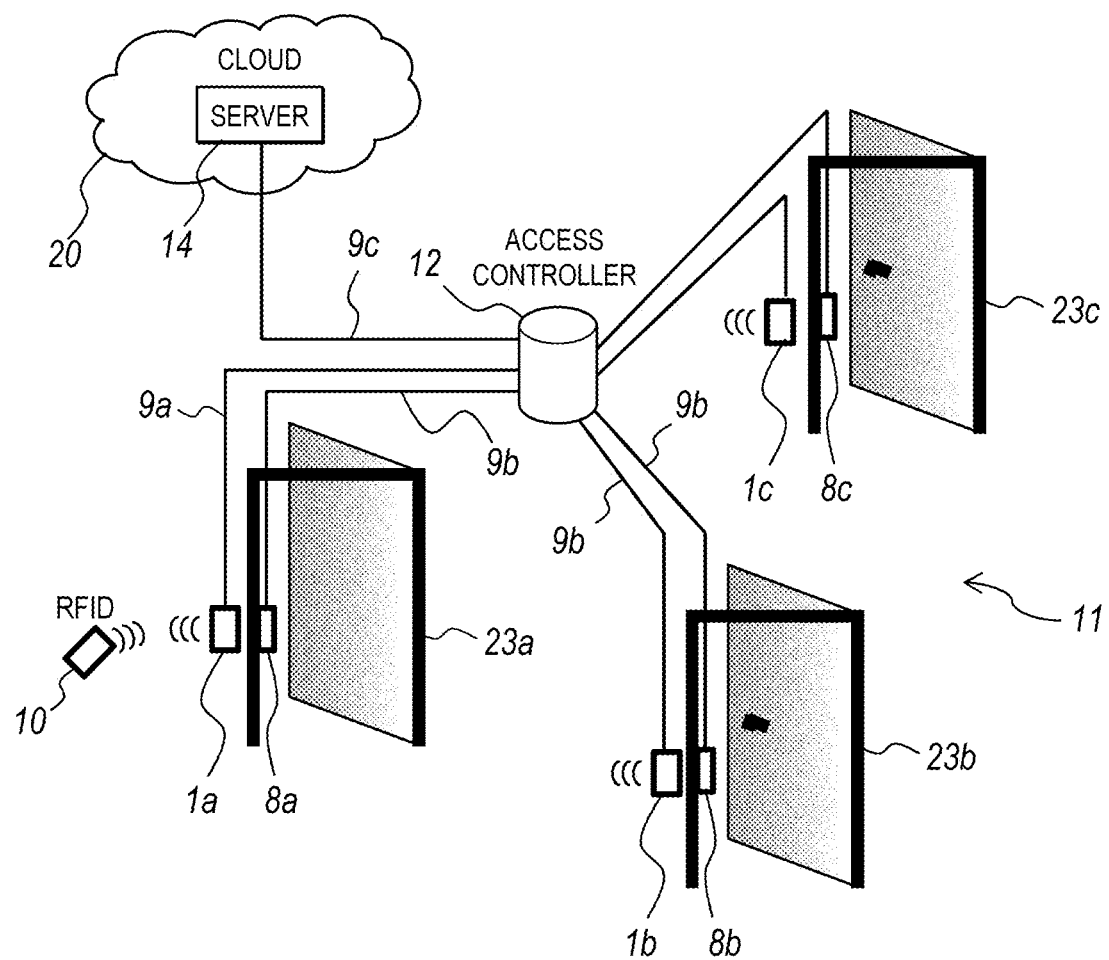
FIG. 1 is a schematic diagram of a physical access-control system according to the prior art.
Figure 2:
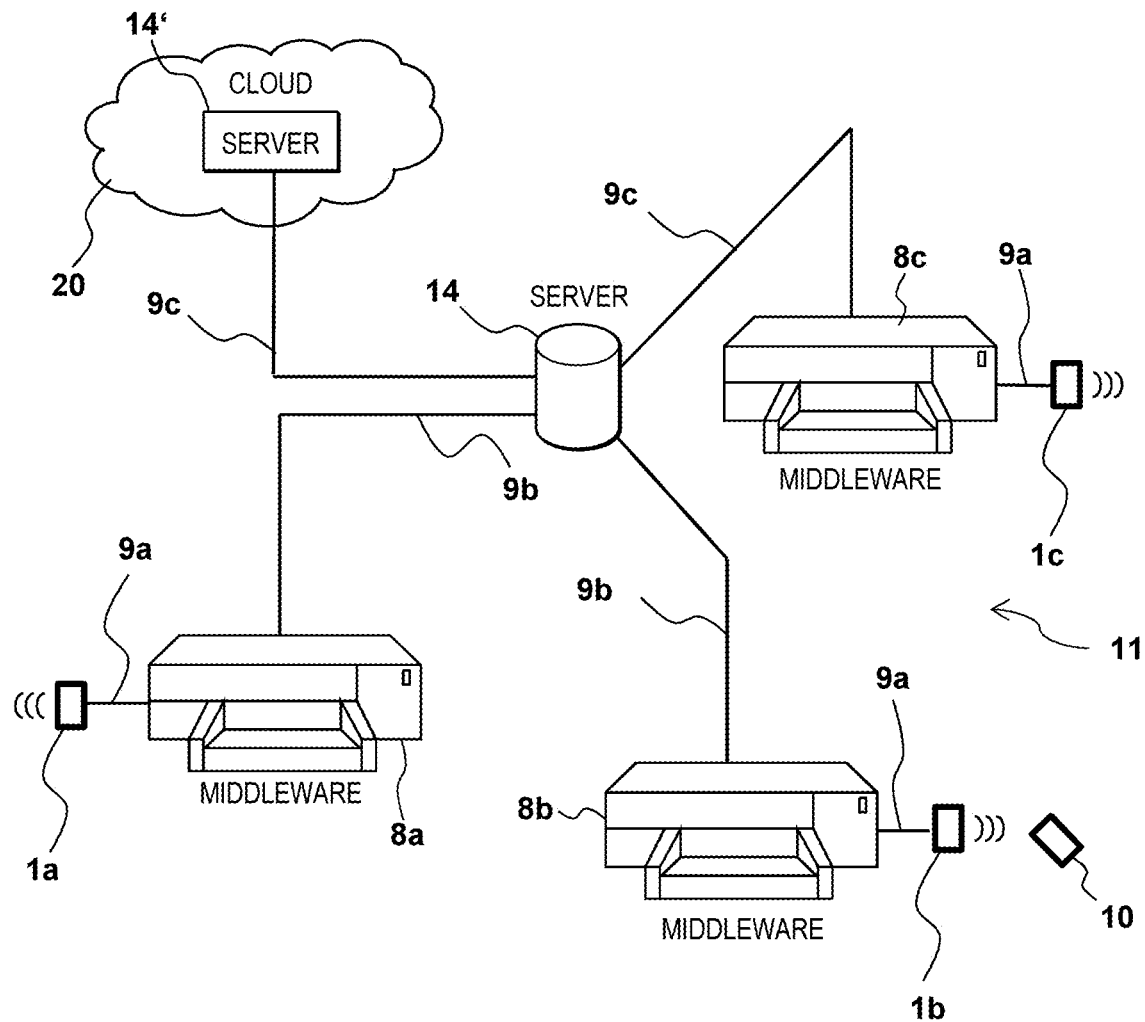
FIG. 2 is a schematic diagram of a printer access-control system according to the prior art.
Figure 9:
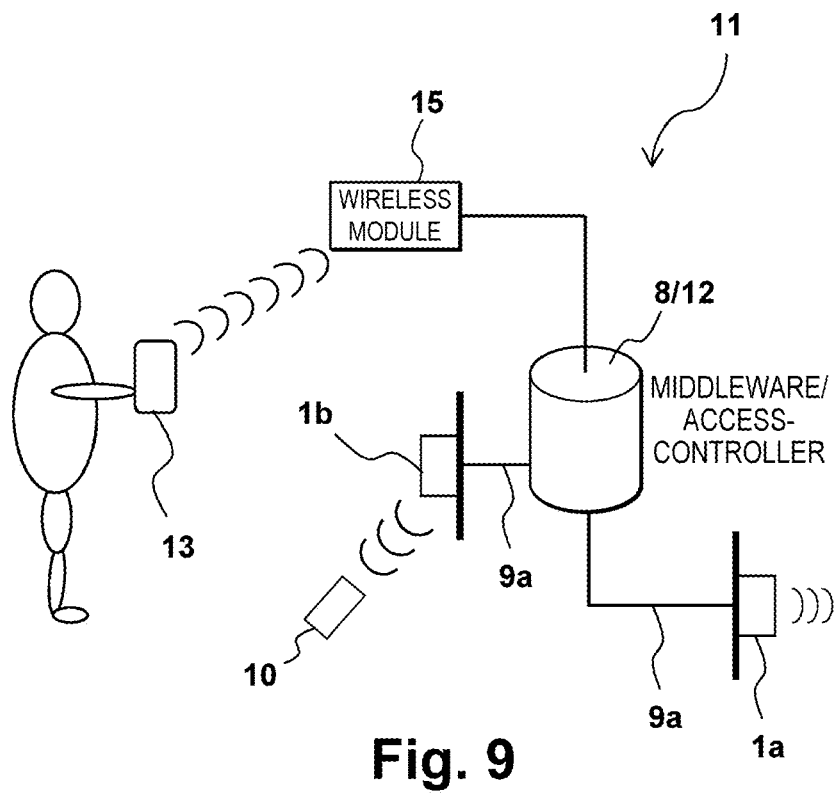
FIG. 9 is a functional block diagram of a sixth embodiment of the access-control system.
Figure 10:
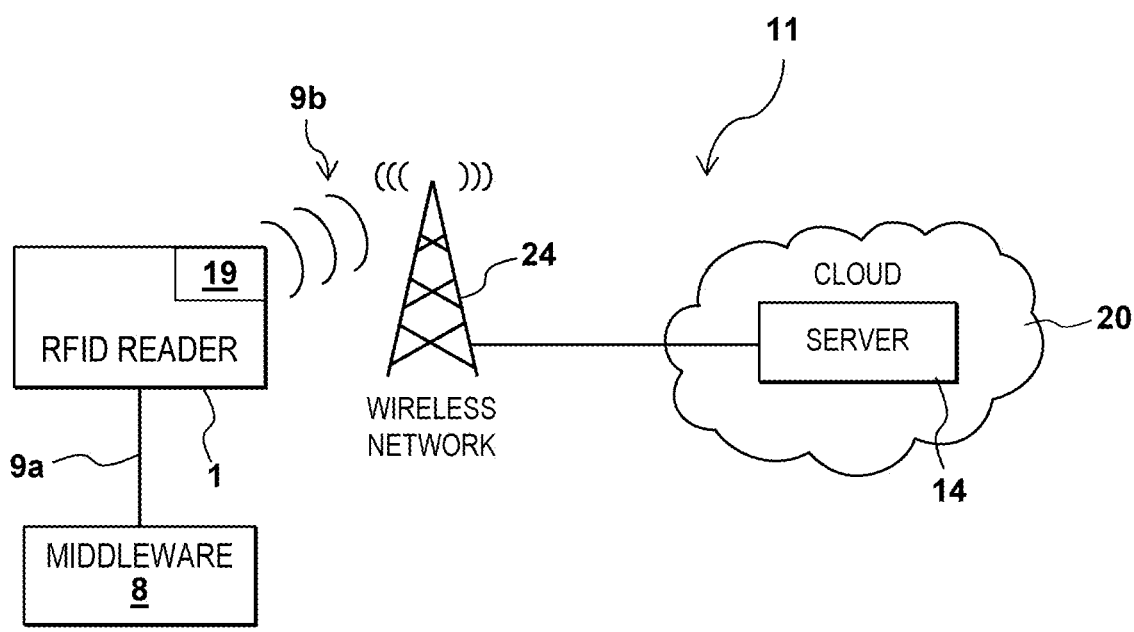
FIG. 10 is a functional block diagram of a seventh embodiment of the access-control system.
Figure 11:
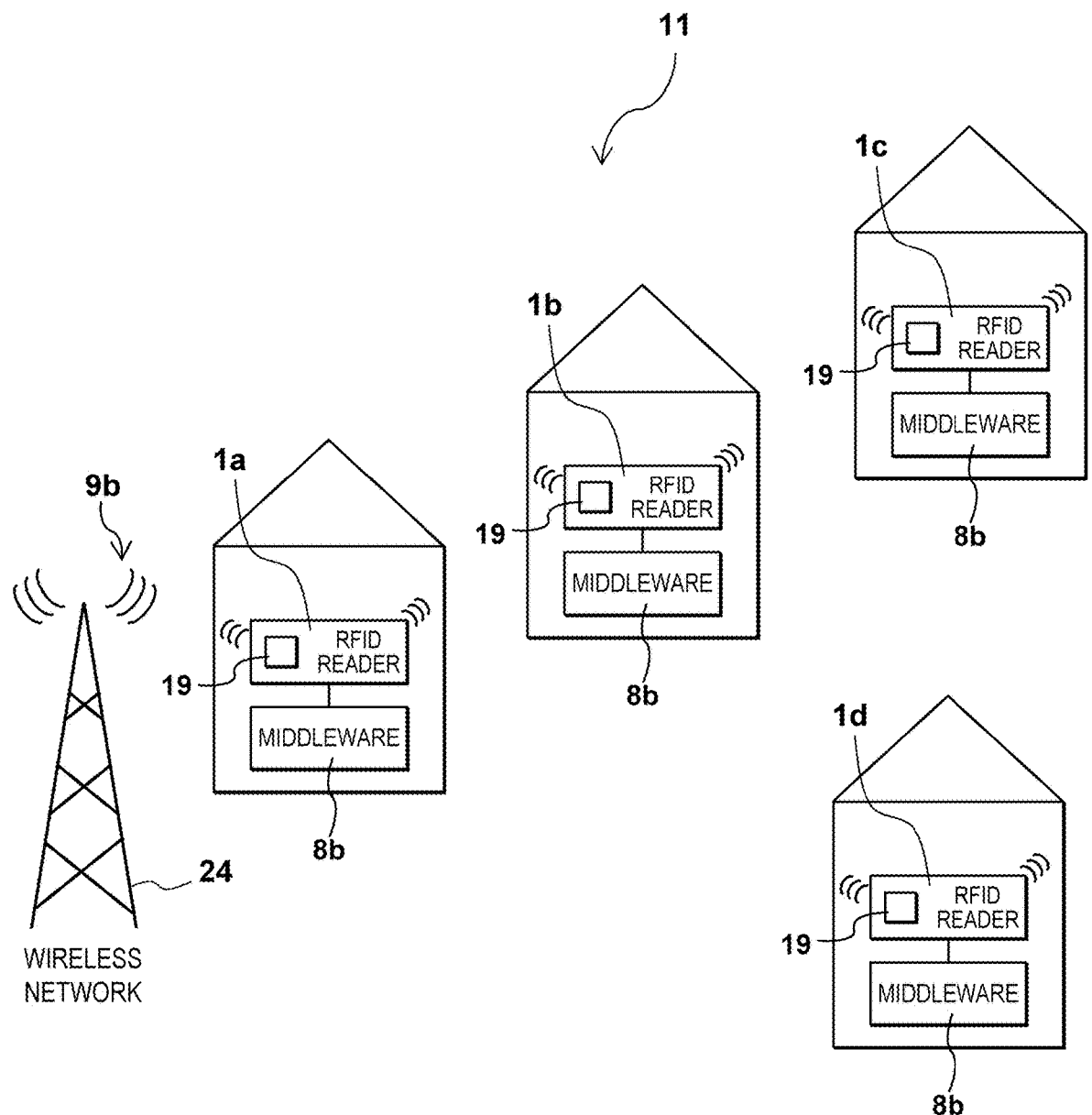
FIG. 11 is a functional block diagram of an eighth embodiment of the access-control system.

The general setup of an access-control system 11 for carrying out a method 100 for updating or upgrading firmware of an RFID reader 1 may preferably be configured as shown in FIGS. 1 and 2 with respect to the prior art, or preferably as shown in FIGS. 9, 10 and 11.

Furthermore, the characteristics of these different setup approaches can preferably be mixed. For example, an access-control system 11 according to FIG. 9 can as well be connected via a data connection to a server, particularly a cloud server. Based on these existing or novel configurations of access-control systems, the inventive RFID reader 1, the inventive access-control system 11 and the inventive method 100 for updating or upgrading firmware of such an RFID reader 1 are implemented.

Figure 3:
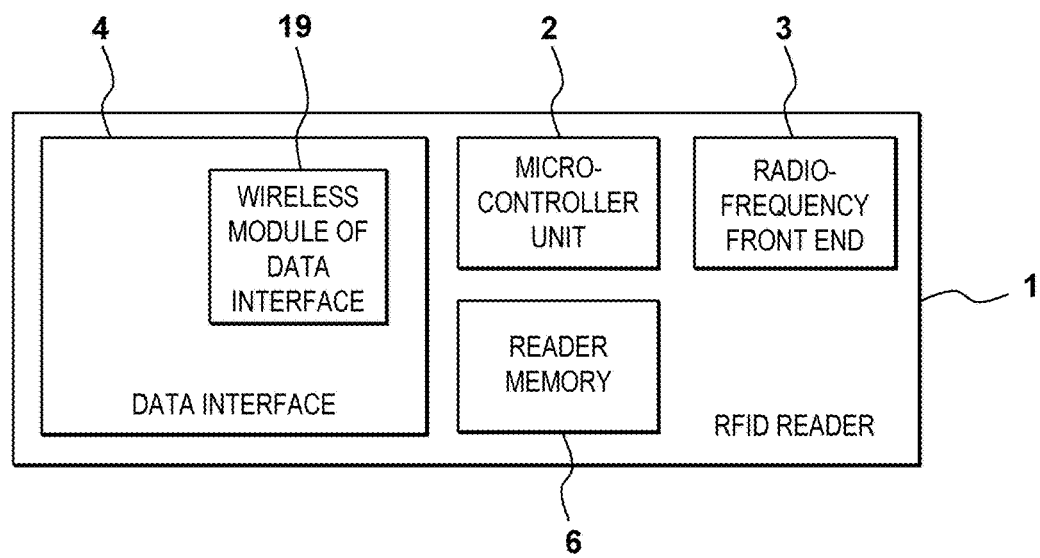
FIG. 3 is a functional block diagram of one embodiment of an RFID reader according to the invention.

FIG. 3 depicts a RFID reader 1 according to the present invention. The RFID reader has a microcontroller unit 2, a radio frequency front end 3, and a data interface 4, and a memory 6.

The microcontroller 2 is configured to automatically check via the data interface 4 whether an update file 5 is stored in a designated storage location whose access address is predefined in the microcontroller unit 2, to automatically, if an update file 5 (not shown) is found, read the update file 5, and to automatically perform an update process of its firmware based on the update file 5. To execute these functions, the microcontroller unit 2 preferably comprises several modules (not shown). For example, the module preferably comprises one module to check, one module to read, and one module to perform an update process. Further preferably, the microcontroller unit 2 has memory module. Preferably, this memory module serves as a program memory where the microcontroller unit 2 boots from.

The radio frequency front end 3 is adapted to communicate via an RFID frequency and protocol with other RFID devices, such as a RFID chip 10 preferably comprised in a RFID tag or a RFID card.

The data interface 4 is preferably configured to communicate with an external device, such as a middleware 8 (not shown), to be controlled by the RFID reader 1, or an access controller 12 (not shown). The data interface 4 may be configured to communicate via USB or any other parallel or serial bus protocol. The data interface 4 may have two separate connecting ports so that the RFID reader 1 can communicate, on the one hand, with a middleware 8 and, on the other hand, for example, with an access-controller 12. In one embodiment of the reader 1, which is especially suited to be employed in an access-control system 11 according to the embodiments of FIG. 10 or 11, the data interface 4 comprises a wireless module 19 that communicates with a wireless network 24 (shown schematically). Such wireless module may be a long-range radio network (LoRa/LNR) module, or a mobile communication device 13.

The memory 6 of the RFID reader 1 may preferably be an EEPROM or Flash memory. This memory may be integrated in the microcontroller unit 2 or may be a memory external to the microcontroller unit 2.

The microcontroller unit 2 has a temporary memory, and particularly a random-access memory (RAM).

Preferably, the microcontroller unit 2 is further configured to automatically check at step 105 (referring to the flowchart of operations in the method shown in FIG. 14, described in further detail below) whether a content of an update file 5 fits its firmware. Further preferably, the microcontroller unit 2 is configured to read at step 106a an update file 5 and initialize an update process. Furthermore, the microcontroller unit 2 is further preferably configured to discard or ignore at step 107b an update file.

Further preferably, the microcontroller unit 2 is configured or has a module to check at step 107 whether an update file is larger than a first remaining space of a program memory of the microcontroller unit 2 not being occupied by the existing operating system. Furthermore, the microcontroller unit 2 is preferably further configured or has a module to perform at step 108a-2 an update process based on the intermediate operating system file.

In a further preferred exemplary embodiment, the microcontroller unit 2 is further configured or comprises a module to send at step 111 assignments to middleware 8 controlled by the respective reader 1 via a server 14. Preferably, the microcontroller unit 2 is further configured or comprises a module to distribute at step 109 an update file to other readers in an access control system 11.

Figure 4:
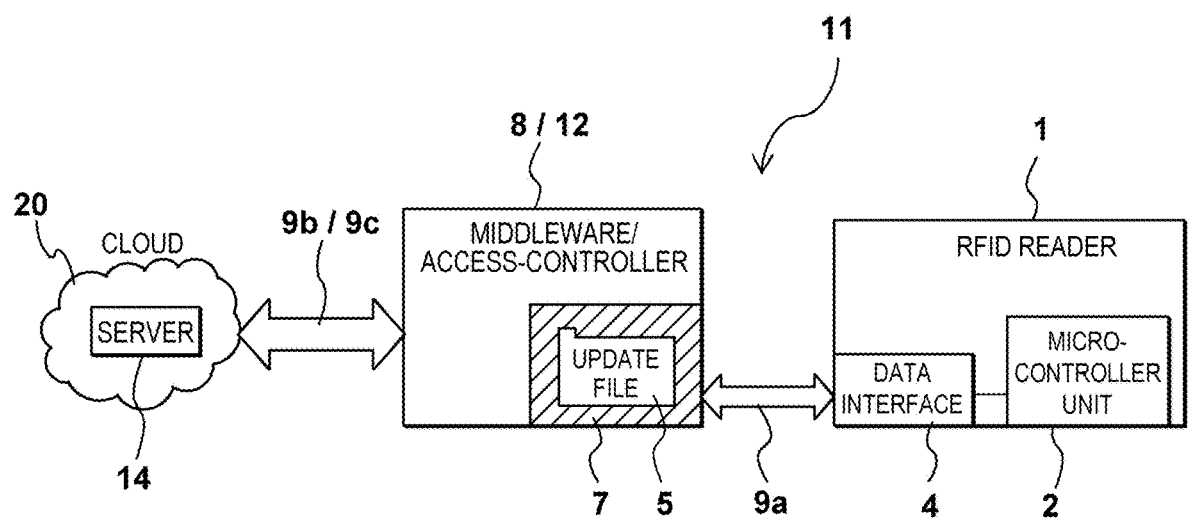
FIG. 4 is a functional block diagram of one embodiment of an access-control system of the invention.

FIG. 4 depicts a functional block diagram of a first embodiment of an access control system 11 for carrying out the method for updating or upgrading firmware of an RFID reader 1 as described with respect to FIG. 3.

In this first embodiment, the designated storage location, whose access address is predefined in the microcontroller 2, is arranged as memory 7 in the middleware 8, for example a printer. The RFID reader 1 is connected to the middleware 8 via the data interface 4 and a data connection 9a. This data connection 9a preferably uses the Open Supervised Device Protocol (OSDP) or the RS485 protocol or the TCP/IP protocol. The middleware 8 is connected via a data connection 9b and/or a data connection 9c to an access-controller 12 or to a central IT server, preferably located in the cloud 20, or a printer server 14.

Figure 14:
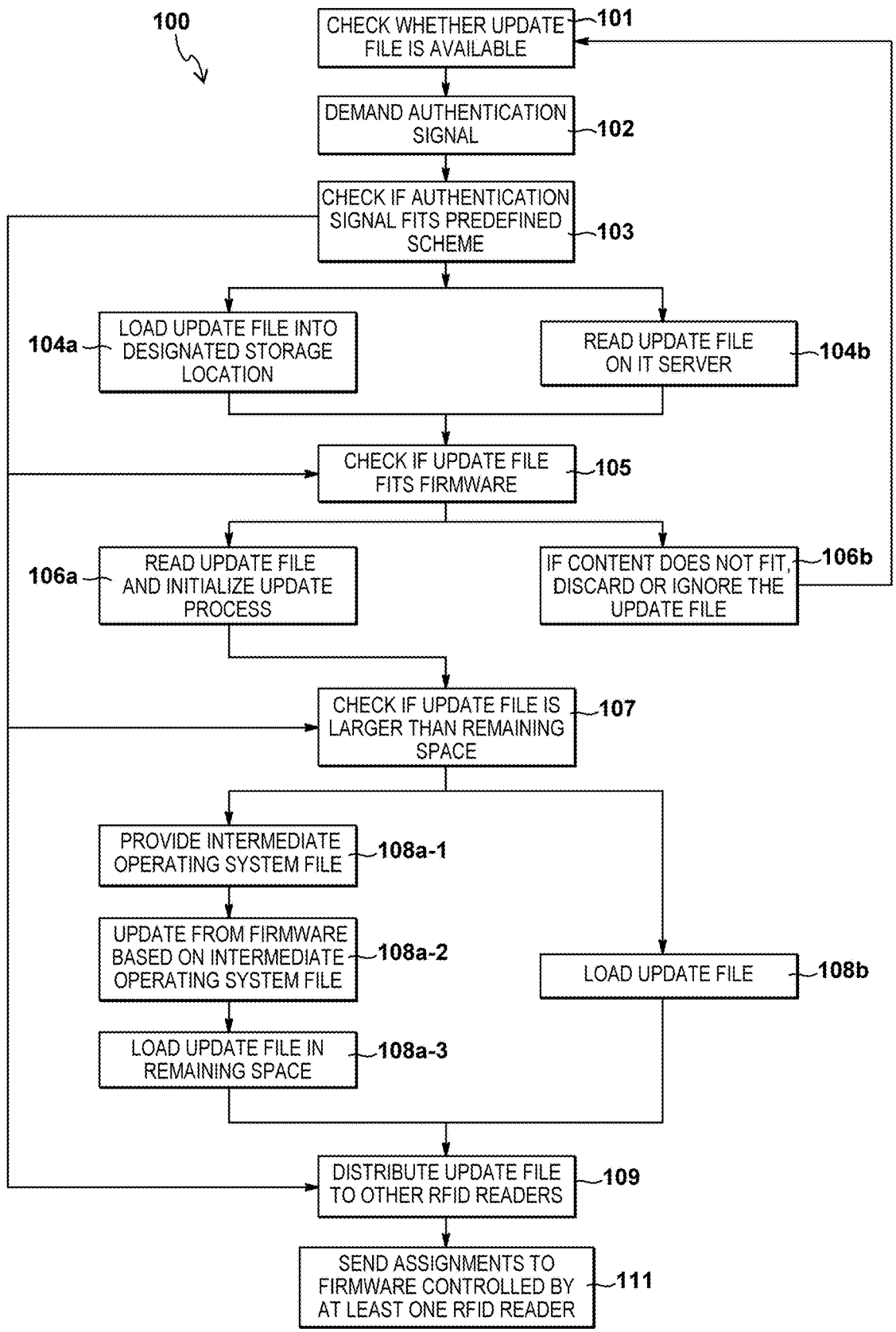
FIG. 14 is a flowchart illustrating an exemplary sequence of steps of the method according to an embodiment of the invention.

Based on this configuration, an exemplary inventive method for updating or upgrading the firmware of the RFID reader 1, also represented in the flowchart of FIG. 14, is as follows:

The microcontroller unit 2 of the RFID reader 1 checks at step 101 periodically whether an update file 5 is provided in the memory 7 of the middleware 8. If no update file 5 is found, the RFID reader 1 continues its normal operation.

If an upgrade or update is envisaged, the central IT server 14 or the access-controller 12 pushes or sends at step 104a an update file 5 over the data connection 9b and/or the data connection 9c to the memory 7 in the middleware 8 serving as designated storage location for the RFID reader 1.

The update file 5 may preferably also be pushed by the central IT server 14 via the access-controller 12 in the memory 7 of the middleware 8. Alternatively, the access-controller 12 pushes the update file in the memory 7 of the middleware 8.

In a preferred sub-routine, as shown in the flow diagram of FIG. 14, the access-controller or the server 14, pushing at step 104a the update file 5 in the designated storage location, may demand at step 102 an authentication signal from the at least one RFID reader 1. The RFID reader 1 then sends out the authentication signal, preferably comprising an ID and/or serial number. The access-controller 12 or the server 14 then receives this authentication signal and checks at step 103 whether this authentication signal fits within a pre-defined scheme. Alternatively, the reader 1 sends the authentication signal without any demand at step 102. The pre-defined scheme may preferably identify a class of RFID readers 1a, 1b, 1c to be updated or upgraded or a single reader 1 which must be activated for a special type of protocol. Further preferably, the authentication signal or the predefined scheme identify a customer to which the reader 1 was sold and/or a use case or application of the reader. Only if the received authentication signal fits to the pre-defined scheme, the access-controller 12 or the server 14 are then loading at step 104a the update file 5 in the designated storage location of the RFID reader 1 or the RFID readers 1a, 1b, 1c.

Additional to the authentication, an authorization may be required for the reader 1 to access the designated storage location and/or read the update file. For this, a username and password are preferably stored in the microcontroller unit 2.

As a further preferred sub-routine of the inventive method 100 also represented in the flow diagram of FIG. 14, the microcontroller unit 2 may check at step 105 whether the content of the update file 5 in the designated storage location, in FIG. 4 the memory 7 of the middleware 8 fits its firmware. If the content fits, the microcontroller unit 2 reads at step 106a the update file 5 and initializes the update or upgrade process at step 106a. Further, if the content does not fit, the microcontroller unit 2 discards or ignores at step 106b the update file 5. In this case, as indicated in the flow diagram of FIG. 14, the microcontroller unit 2 steps back and checks again automatically, whether a new update file 5 is stored in the designated storage location, in the case of FIG. 4 the memory 7 of the RFID reader 1.

Figure 12:
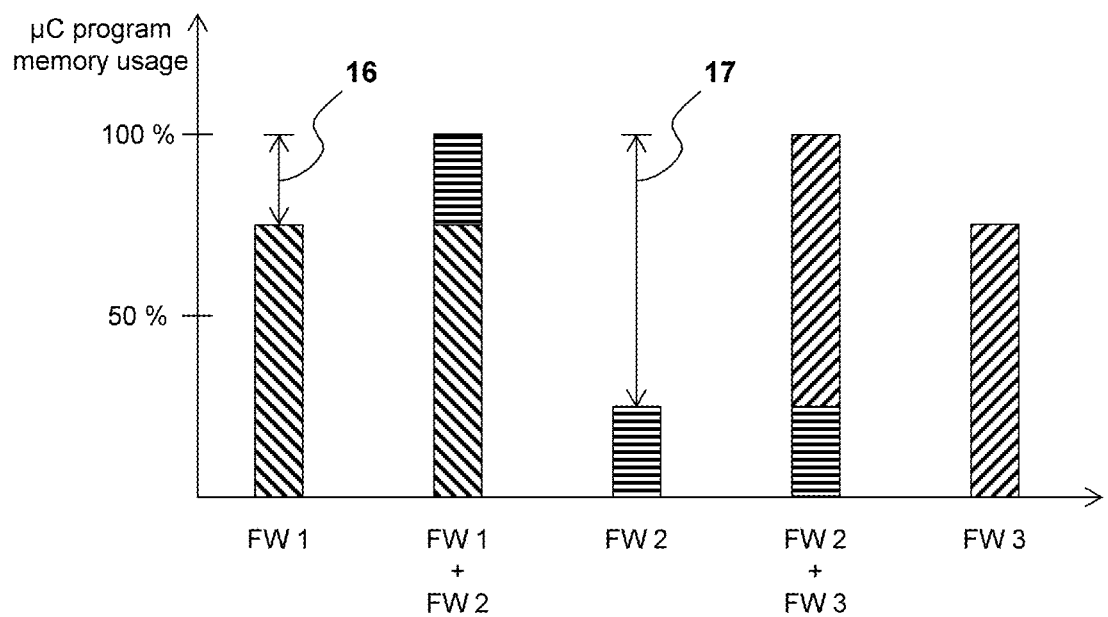
FIG. 12 is a graphical representation of storage management according to one embodiment of a method according to the invention.
Figure 13:
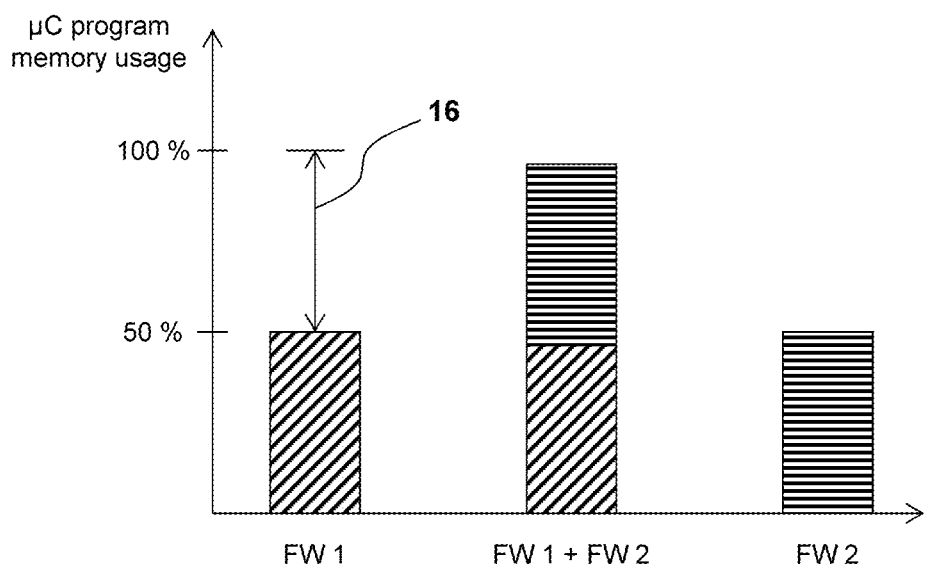
FIG. 13 is a graphical representation of storage management under another embodiment of the method.

In a further preferred subroutine, the inventive method 100 may include a process for a storage management of a program memory of the microcontroller unit 2 of the RFID reader 1 depicted in FIG. 12 and FIG. 13 and represented in the flow diagram of FIG. 14.

Such a subroutine becomes necessary in access control systems 11, where the update file 5 and/or the updated or upgraded firmware may necessitate more storage capacity as initially estimated when designing the program memory of the microcontroller unit 2. The program memory of a microcontroller unit 2 serves generally to host the operating system and can be designed as a ROM-memory or Flash-ROM-memory.

In this subroutine, the microcontroller unit 2 checks at step 107 automatically whether the update file 5 is larger than a first remaining space of a program memory not being occupied by the existing operating system. If the update file 5 is larger than the first remaining space 16, the microcontroller unit 2 preferably automatically transmits an error message to an access-controller 12 or a central IT server 14 indicating that an automatic update or upgrade of the firmware is not possible.

Preferably, the access-controller 12 or the central IT server 14, in the case that the update file 5 is larger than the first remaining space 16, provides at step 108a-1 an intermediate operating system file in the designated storage location, in FIG. 4 the memory 7 in the middleware 8. The microcontroller unit 2 finds this intermediate operating system file when checking at step 101 again for an update file 5, loads the intermediate operating system file in its program memory and performs at step 108a-2 an update process of its firmware based on the intermediate operating system file. When the RFID reader runs on the intermediate operating system, the microcontroller unit 2 loads at step 108a-3 the update file 5 in a second remaining space 17 of the program memory not being occupied by the intermediate operating system. This part of the sub-routine is depicted in FIG. 12.

An alternative part of the sub-routine, if the update file 5 equals or is smaller than the first remaining space 16, is represented on the contrary in FIG. 13. In this case, the update file is loaded at step 108b in the first remaining space 16 without any further steps.

The above described two parts of the sub-routine shown in FIGS. 12 and 13 assure that an RFID reader 1 does not crash during an update or upgrade process due to an incomplete operating system being loaded in the program memory.

Figure 5:
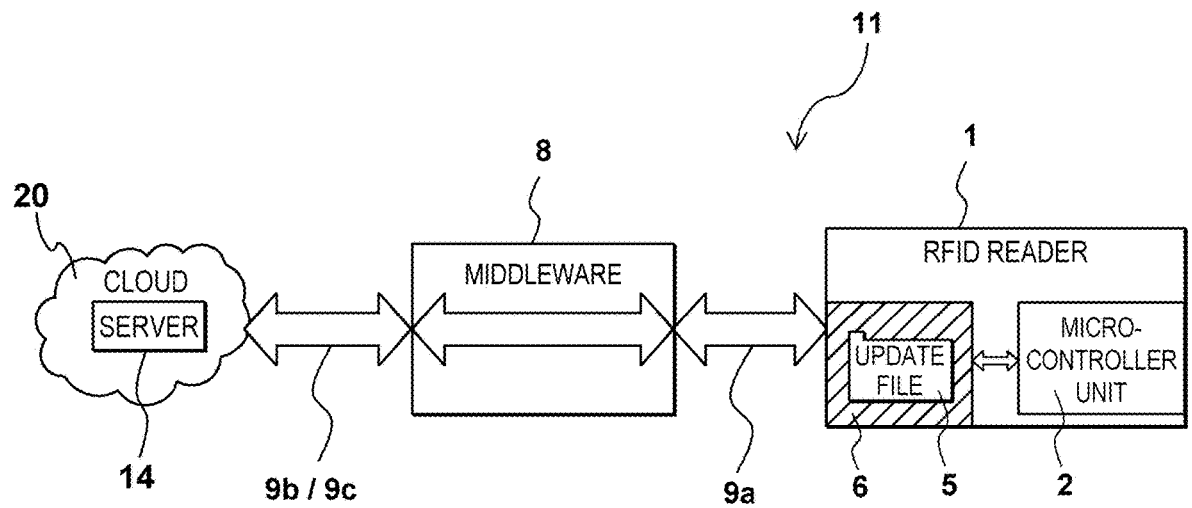
FIG. 5 is a functional block diagram of a second embodiment of the access-control system.

FIG. 5 depicts a functional block diagram of a second embodiment of an access control system 11 for carrying out the method 100 for updating or upgrading firmware of an RFID reader 1 as described with respect to FIG. 4.

In contrast to the first embodiment, the designated storage location of the microcontroller unit 2 of the reader 1 is a memory, preferably a Flash memory or an EEPROM in the RFID reader 1. In this embodiment, the microcontroller 2 checks within this memory 6 whether an update file 5 exists in the memory 6.

Such an update file 5 may be pushed at step 104a by a central IT server 14 via a middleware, such as a printer 8 or an access-controller, directly in the memory 6. Alternatively, the IT server 14 hands the update file 5 on to the middleware 8 or the access-controller 12, which then pushes at step 104a the update file 5 in the memory 6 of the RFID reader 1.

For the rest, the inventive method is operated by the second embodiment of the access control system 11 of FIG. 5, the same as in the first embodiment.

Figure 6:
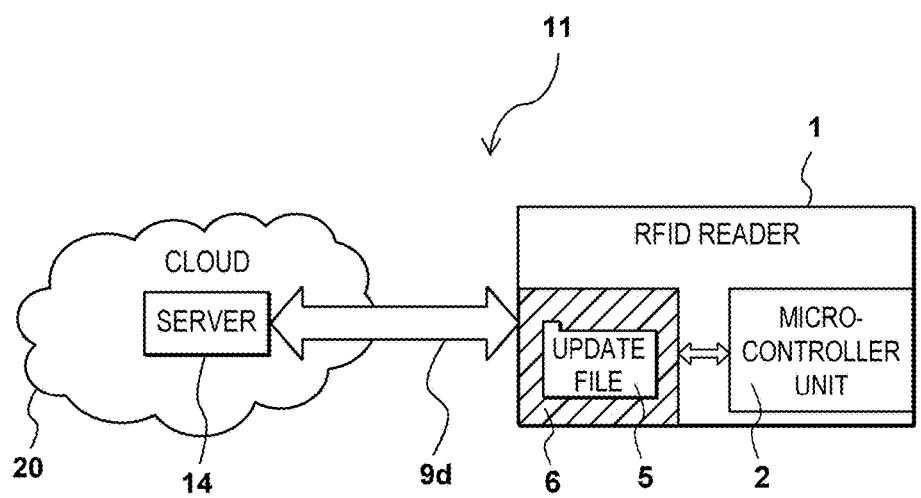
FIG. 6 is a functional block diagram of a third embodiment of the access-control system.

FIG. 6 depicts a functional block diagram of a third embodiment of an access-control system 11 for carrying out the inventive method 100.

In contrast to the second embodiment, RFID reader 1 has, via its data interface 4 (not shown), a direct data connection 9d, preferably a wireless data connection, with server 14, particularly a cloud server. Therefore, the server 14 can push at step 104*a* the update file 5 directly in the memory 6 of the RFID reader 1.

As described with respect to the second embodiment, the microcontroller 2 then checks at step 101 within the memory 6 of the RFID reader 1 whether an update file 5 is available.

For the rest, the method 100 for carrying out an update or upgrade process of the firmware of the RFID reader 1 is performed, as described with respect to the first and second embodiments.

Figure 7:
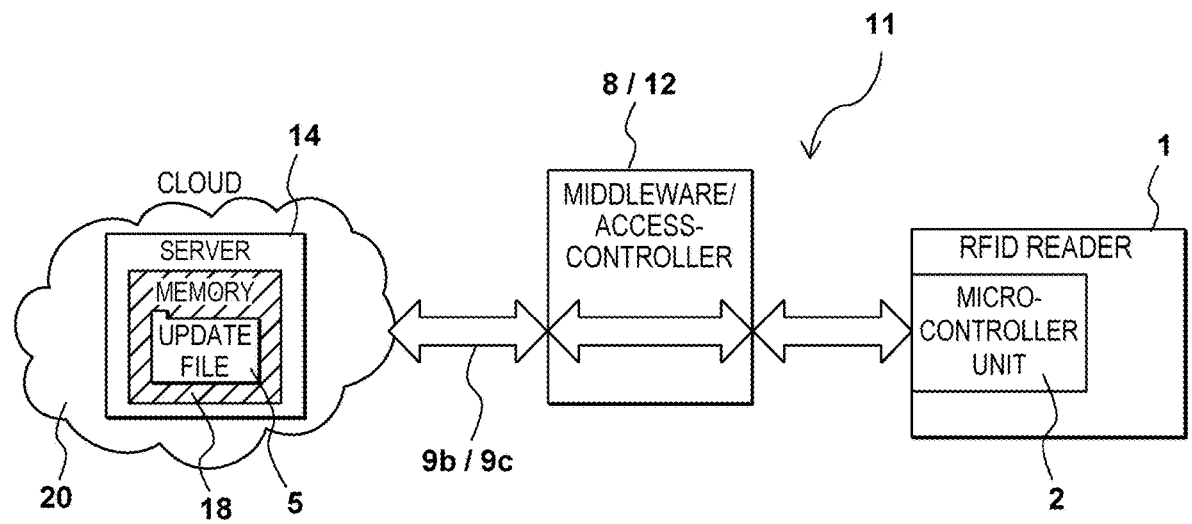
FIG. 7 is a functional block diagram of a fourth embodiment of the access-control system.

FIG. 7 depicts a functional block diagram of a fourth embodiment of an access-control system 11 for carrying out the inventive method 100.

In contrast to the first embodiment, the designated storage location in this case is a memory 18 in the central IT server 14 and not in the middleware 8 or an access-controller 12.

In contrast to the embodiments described above, the update file 5 does not have to be pushed in a memory of another device. Instead, the designated storage location checked at step 101 by the microcontroller unit 2 is the memory 18 in the central IT server 14. In case that the update file 5 is applicable to the RFID reader 1, the microcontroller 2 reads at step 104*b* the update file 5 on the IT server 14.

Figure 8:
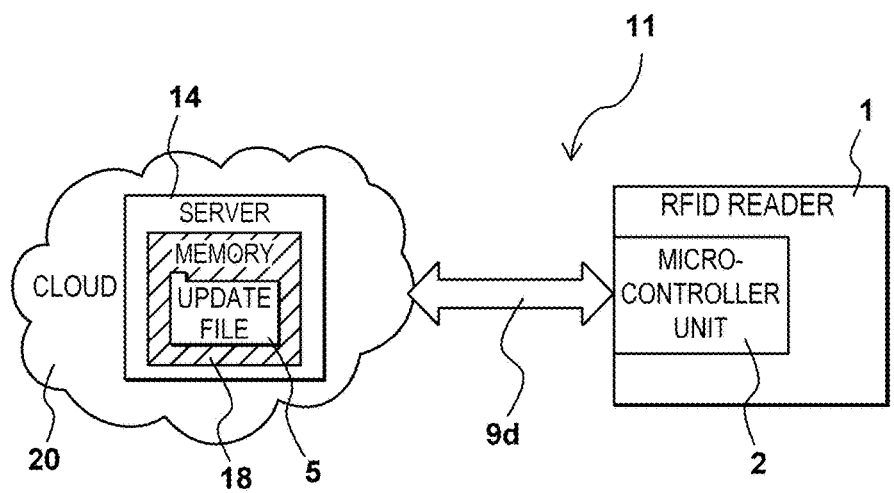
FIG. 8 is a functional block diagram of a fifth embodiment of the access-control system.

FIG. 8 depicts a functional block diagram of a fifth embodiment of an access control system 11 for carrying out the inventive method 100.

In contrast to the fourth embodiment 7, the central server 14 and the RFID reader are directly connected via a data connection 9*d* and, as in the third embodiment, the data interface 4 (not shown) is a wireless communication interface.

In contrast to the fourth embodiment, there is no intermediary of a middleware 8 or an access-controller 12 in the data communication between the RFID reader 1 and a central IT server 14.

Similar as in the fourth embodiment, the microcontroller unit 2 checks at step 101 and, if applicable, reads at step 106 the update file 5 in the memory 18 of the central server 14 without the need for the server to push the file in another designated storage location.

In the configuration of the third embodiment according to FIG. 6 or the fifth embodiment according to FIG. 8 of an access-control system 11, the middleware 8, such as a printer or a door opener, may preferably be controlled by the RFID reader 1 by the central server 14. For this, the respective middleware 8 must be connected with a further data connection (not shown) to the server 14. In this case, the inventive method 100 preferably comprises a further step of at least one reader 1 sending 111 assignments to a firmware controlled by at least one reader 1 via the server 14.

FIG. 9 depicts a functional block diagram of a sixth embodiment of an access-control system 11 for carrying out the inventive method 100.

In this embodiment, the access-control system 11 further has a wireless module 15. Via this wireless module 15, an update file 5 may be loaded, for example via a mobile communication device 13, e.g. a smart phone, into the access-control system 11, the mobile communication device 13 in turn uses Wi-Fi or GSM or other mobile communication protocols to connect to a server 14 (not shown). This update file 5 is stored in the designated storage location, for example in a middleware 8, or an access-controller 12, or in at least one of the readers 1*a*, 1. The wireless module 15 may be part of the middleware 8, an access controller 12, or at least one of the RFID readers 1*a*, 1*b*.

Alternatively, at least one of the RFID readers 1*a*, 1*b* may be configured to load an update file 5 from an RFID chip 10 comprised in a tag or card. This update file 5 can then be stored in a designated storage location in at least one of the readers 1*a*, 1*b*, or the middleware 8, or an access-controller 12. Based on this update file 5, an inventive method 100 for updating or upgrading the firmware of the at least one reader 1*a*, 1*b* can be carried out.

The middleware 8 and/or the access-controller 12 may preferably be also connected to a server 14, in particular a cloud server 14. In this case, the designated storage location can also be located in the server 14.

FIG. 10 depicts a configuration of a seventh embodiment of an inventive access-control system 11.

In this embodiment, the direct data connection 9*d* between a central IT server 14 and an RFID reader 1 can be established via a wireless data connection, such as a long-range radio network, preferably a LoRa- and/or a mobile communication protocol. For this, the central data server 14 is connected to an antenna 24 and an RFID reader 1 has a wireless module 19 configured to communicate in the same protocol as the antenna 24. The reader 1, on the other hand, is preferably connected then to a middleware 8 via a data connection 9*a*.

FIG. 11 depicts an access-control system 11 with a multitude of RFID readers 1*a*, 1*b*, 1*c*, 1*d*, wherein at least one reader 1*a* is adapted to communicate over a long-range radio network protocol data connection 9*d*, as shown in FIG. 10.

Via the long-range radio network protocol data connection 9*d*, an update file can be loaded to a designated storage location in a first RFID reader 1*a*. This first RFID reader 1*a* may serve as a node in a mesh network and distribute the update file 5 to designated storage locations within the other readers 1*b*, 1*c*, 1*d* of the mesh network. For this, a wireless data connection may be established by wireless modules 19 within every reader 1*a*, 1*b*, 1*c*, 1*d*.

Alternatively, only reader 1*a* has a wireless module 19 to communicate over the long-range radio network protocol, while the other readers 1*b*, 1*c*, 1*d* are instead connected to the first RFID reader 1*a* by a wired data connection.

It is understood by the person skilled in the art that the embodiments which are described in the foregoing are only examples which do not limit the scope of protection, the application fields and the configuration of the inventive method 100 and systems 11 as described below. Particularly, the order of the method steps is not limited to the exemplary order depicted in FIG. 14. Furthermore, as indicated by the flashes, particularly several intermediary steps may be omitted without failing to achieve at least some effects of the invention. Furthermore, the foregoing description shall provide the person skilled in the art a guideline for the realization of at least one working example of the invention, wherein changes, in particular with respect to the function and the arrangement of the described components, can be established without departing from the scope of protection defined by the claims and feature combinations equivalent to this scope of protection.

The embodiments described above are only descriptions of preferred embodiments of the present invention, and do not intended to limit the scope of the present invention. Various variations and modifications can be made to the technical solution of the present invention by those of ordinary skills in the art, without departing from the design and spirit of the present invention. The variations and modifications should all fall within the claimed scope defined by the claims of the present invention.

REFERENCE NUMERALS

Reader 1
Microcontroller unit 2
Radio-frequency front end 3
Data interface 4
Update file 5
Reader memory 6
Access-controller/Middleware memory 7
Middleware 8, 8a, 8b, 8c
Data connection 9a, 9b, 9c, 9d
RFID Chip 10
Access control system 11
Access-controller 12
Mobile communication device 13
Server 14
Wireless module of Access-controller 15
First remaining storage capacity 16
Second remaining storage capacity 17
Server memory 18
Wireless module of data interface 19
Data-Cloud 20
Door 23a, 23b, 23c
Wireless network 24
Method 100
Steps of the method 101-111

What is claimed is:

1. A method for updating or upgrading firmware of a radio frequency identification (RFID) reader installed in an access control system for controlling middleware, wherein the access control system comprises at least one RFID reader, a middleware, an access-controller device, and a server, and wherein the at least one RFID reader has a microcontroller unit, the method comprising:
the server pushing an update file for the at least one RFID reader in at least one of a memory of the access-controller device and a memory of the middleware, which is provided as a designated storage location, wherein an access address of the designated storage location is predefined in the microcontroller unit;
the microcontroller unit checking periodically whether the update file is stored in the designated storage location;
if the update file is found, the microcontroller unit automatically reading, the update file;
the microcontroller unit automatically performing an update or upgrade process of its firmware based on the update file;
sending an authentication signal by the at least one RFID reader;
receiving and checking the authentication signal of the at least one RFID reader by the middleware, the access-controller device or the server; and
only if the received authentication signal fits to a predefined scheme, pushing the update file matching the at least one RFID reader in the designed storage location;
wherein the authentication signal and the predefined scheme holds information on a use case or application of the at least one RFID reader or a customer using the at least one RFID reader.

2. The method of claim 1, further comprising:
determining the update file matching the at least one RFID reader from a plurality of update files based on the authentication signal.

3. The method of claim 2, wherein the access-controller device broadcasts the update file to a plurality of RFID readers.

4. The method of claim 1, further comprising:
checking, by the microcontroller unit, whether a content of the update file fits its firmware;
if the content fits, reading, by the microcontroller unit, the update file and initializing the update or upgrade process; and
if the content does not fit, discarding or ignoring, by the microcontroller unit, the update file.

5. The method of claim 1, further comprising:
checking, by the microcontroller unit, whether the update file is larger than a first remaining space of a memory of a program memory of the microcontroller unit not being occupied by an existing operating system;
if the update file is larger than the first remaining space, providing or loading an intermediate operating system file that fits in the first remaining space; performing an update process of its firmware based on the intermediate operating system file; and loading the update file in a second remaining space of the program memory of the designated storage location not being occupied by the intermediate operating system file; and
if the update file equals or is smaller than the first remaining space, loading the update file in the first remaining space.

6. The method of claim 1, wherein a data connection between the at least one RFID reader and the middleware is established via the server, and the method further comprises:
sending, by the at least one RFID reader, assignments to the middleware controlled by the at least one RFID reader via the server.

7. The method of claim 1, further comprising:
distributing, by the at least one RFID reader, the update file to other readers in the access control system.

8. A radio frequency identification (RFID) reader, comprising:
a microcontroller unit,
a radio-frequency front end, and
a data interface,
wherein a server pushes an update file for the RFID reader in at least one of a memory of an access-controller device and a memory of a middleware, which is provided as a designated storage location, wherein an access address of the designated storage location is predefined in the microcontroller unit,
wherein the microcontroller unit is configured to carry out a method comprising:
checking periodically, via the data interface, whether the update file is stored in the designated storage location;
if the update file is found, automatically read the update file; and
automatically perform an update process of its firmware based on the update file;
wherein the at least one RFID reader sends an authentication signal;
wherein the middleware, the access controller device or the server receives and checks the authentication signal of the at least one RFID reader;
wherein only if the received authentication signal fits to a predefined scheme, the update file matching the at least one RFID reader is pushed in the designed storage location; and
wherein the authentication signal and the predefined scheme holds information on a use case or application of the at least one RFID reader or a customer using the at least one RFID reader.

9. The RFID reader of claim 8, wherein where the designated storage location is a dedicated additional storage element connected to the microcontroller unit, in the form of an external EEPROM or flash memory.

10. The RFID reader of claim 8, wherein the designated storage location is a memory in a printer connected by a data connection to the RFID reader and being controlled by the RFID reader.

11. The RFID reader of claim 8, wherein the data interface has a wireless module configured to communicate in a long-range radio network and/or a mobile communication protocol.

12. An access control system, comprising:
a radio frequency identification (RFID) reader, comprising:
  a microcontroller unit,
  a radio-frequency front end, and
  a data interface,
  wherein a server pushes an update file for the RFID reader in at least one of a memory of an access-controller device and a memory of a middleware, which is provided as a designated storage location, wherein an access address of the designated storage location is predefined in the microcontroller unit,
  wherein the microcontroller unit is configured to carry out a method comprising:
    checking periodically, via the data interface, whether the update file is stored in the designated storage location;
    if the update file is found, automatically read the update file; and
    automatically perform an update process of its firmware based on the update file, and
  the middleware in the form of a printer, being controlled by the RFID reader,
  wherein the designated storage location is a memory in an access-controller device or a memory in the middleware,
  wherein the RFID reader sends an authentication signal;
  wherein the middleware, the access controller device or the server receives and checks the authentication signal of the RFID reader;
  wherein only if the received authentication signal fits to a predefined scheme, the update file matching the RFID reader is pushed in the designed storage location; and
  wherein the authentication signal and the predefined scheme holds information on a use case or application of the RFID reader or a customer using the RFID reader.

13. The access control system of claim 12, further comprising:
  the access-controller device, which is in the form of a physical access control (PAC), and which is connected to the RFID reader via a data connection.

14. The access control system of claim 12, wherein the RFID reader is configured to act as an access point for a mesh-network between a plurality of readers.

15. The access control system of claim 12, wherein the access-controller has a Wi-Fi- or Bluetooth-module and the data connection between the server and the access-controller is established via the Wi-Fi- or Bluetooth-module.

* * * * *